US012605224B2

(12) United States Patent　　　(10) Patent No.:　US 12,605,224 B2
Kwon et al.　　　　　　　　　　　(45) Date of Patent:　Apr. 21, 2026

(54) APPARATUS FOR LOCKING SURGICAL INSTRUMENT BY USING MAGNETIC FORCE

(71) Applicants:ROEN SURGICAL INC., Daejeon (KR); KOREA ADVANCED INSTITUTE OF SCIENCE AND TECHNOLOGY, Daejeon (KR)

(72) Inventors: Dong-Soo Kwon, Daejeon (KR); Un-Je Yang, Daejeon (KR); Duk-Yoo Kong, Daejeon (KR); Duk-Sang Kim, Daejeon (KR)

(73) Assignees: ROEN SURGICAL INC., Daejeon (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 328 days.

(21) Appl. No.: 18/036,871

(22) PCT Filed: Nov. 11, 2021

(86) PCT No.: PCT/KR2021/016390
§ 371 (c)(1),
(2) Date: May 12, 2023

(87) PCT Pub. No.: WO2022/103165
PCT Pub. Date: May 19, 2022

(65) Prior Publication Data
US 2023/0404697 A1　　Dec. 21, 2023

(30) Foreign Application Priority Data
Nov. 13, 2020　(KR) ........................ 10-2020-0151606

(51) Int. Cl.
*A61B 90/00*　　　　(2016.01)
*A61B 17/00*　　　　(2006.01)

(52) U.S. Cl.
CPC .............. *A61B 90/08* (2016.02); *A61B 17/00* (2013.01); *A61B 2017/00876* (2013.01)

(58) Field of Classification Search
None
See application file for complete search history.

(56) References Cited

U.S. PATENT DOCUMENTS

2002/0087166 A1　7/2002　Brock et al.
2011/0301602 A1　12/2011　Roy et al.
(Continued)

FOREIGN PATENT DOCUMENTS

EP　　　　3034019 A1　6/2016
KR　　20130102894 A　9/2013
(Continued)

OTHER PUBLICATIONS

International search report of PCT/KR2021/016390, Mar. 2, 2022, English translation.
(Continued)

*Primary Examiner* — Sana Sahand
(74) *Attorney, Agent, or Firm* — STIP Law Group, LLC

(57)　　　　　　　ABSTRACT

The present invention relates to an apparatus for locking a surgical instrument by using magnetic force and, more specifically, to an apparatus for locking a surgical instrument by using magnetic force, which installs or uninstalls an instrument for microsurgery by using magnetic force in order to reduce a load that may occur during installing/uninstalling an instrument for microsurgery. To this end, disclosed is the apparatus for locking a surgical instrument by using magnetic force, comprising: a first magnetic force unit which forms a locking magnetic force when moving in a locking direction so that an attractive force is applied in a different direction from the locking direction and a locking operation is performed, and forms a release magnetic force when moving in a release direction so that a repulsive force is applied in a different direction from the release direction and an unlocking operation is performed; a second magnetic force unit which is fixed and forms the locking magnetic force and the release magnetic force by interacting with the first magnetic force generation unit; and a locking unit which is locked or unlocked due to the attractive force and (Continued)

the repulsive force generated by the first and second magnetic force units when moving in the locking direction and the release direction, so as to install and uninstall the surgical instrument.

6 Claims, 10 Drawing Sheets

(56)                    References Cited

U.S. PATENT DOCUMENTS

| | | | |
|---|---|---|---|
| 2018/0304475 A1* | 10/2018 | Zachary | B25J 15/0416 |
| 2019/0328419 A1 | 10/2019 | Stulen et al. | |

FOREIGN PATENT DOCUMENTS

| | | |
|---|---|---|
| KR | 101403766 B1 | 6/2014 |
| KR | 101502446 B1 | 3/2015 |
| KR | 101661710 B1 | 10/2016 |
| KR | 101762503 B1 | 7/2017 |
| WO | WO2012058221 A1 | 5/2012 |

OTHER PUBLICATIONS

The extended European search report of EP 21 89 2332, Sep. 5, 2024.
Decision to Grant a Patent of 10-2020-7030143 from Korean Intellectual Property Office, Aug. 5, 2022, English translation.

* cited by examiner (a)

APPARATUS FOR LOCKING SURGICAL INSTRUMENT BY USING MAGNETIC FORCE

CROSS-REFERENCE TO RELATED APPLICATIONS

This application is the U.S. National Phase under 35 U.S.C. § 371 of International Application No. PCT/KR2021/016390, filed on Nov. 11, 2021, which in turn claims the benefit of Korean Application No. 10-2020-0151606, filed on Nov. 13, 2020, the disclosures of which are incorporated by reference into the present application.

TECHNICAL FIELD

The present invention relates to an apparatus for locking a surgical instrument by using magnetic force and, more specifically, to an apparatus for locking a surgical instrument by using magnetic force, which installs or uninstalls an instrument for microsurgery by using magnetic force in order to reduce a load that may occur during installing/uninstalling an instrument for microsurgery.

BACKGROUND ART

Korea Patent Registration No. KR 10-1403766 (Title of invention: Locking apparatus of surgical instruments using magnetic force) discloses that when chucking members are rotated at a predetermined angle, the chucking members are disassembled by repulsive force therebetween, and when rotated at another angle, the chucking members are automatically assembled by an attractive force between magnets so as to automate an assembly and disassembly process of the chucking members.

The related art document, which relates to a method that may simply automate assembly between two parts by using an attractive force and a repulsive force, has a problem in that the related art may not be used as a structure for reducing a load generated during installing and uninstalling of an instrument for microsurgery.

DISCLOSURE OF THE INVENTION

Technical Problem

In order to solve the above-described problem, the present invention provides an apparatus for locking a surgical instrument by using magnetic force in order to maximally reduce a load that may occur during installing/uninstalling an instrument for microsurgery.

The objects of the present invention are not limited to the aforementioned object, but other objects not described herein will be clearly understood by those skilled in the art from descriptions below.

Technical Solution

An embodiment of the present invention provides an apparatus for locking a surgical instrument by using magnetic force, characterized by including: a first magnetic force unit configured to form a locking magnetic force when moving in a locking direction so that an attractive force is applied in a different direction from the locking direction and a locking operation is performed, and form a release magnetic force when moving in a release direction so that a repulsive force is applied in a different direction from the release direction and an unlocking operation is performed; a second magnetic force unit which is fixed and forms the locking magnetic force and the release magnetic force by interacting with the first magnetic force unit; and a locking unit which is locked or unlocked due to the attractive force and the repulsive force generated by the first and second magnetic force units when moving in the locking direction and the release direction, so as to install and uninstall the surgical instrument.

Also, the second magnetic force unit may have magnetic poles that are alternately arranged along a movement direction so that the locking magnetic force and the release magnetic force are formed in the locking direction and the release direction of the first magnetic force unit.

Also, the first magnetic force unit and the second magnetic force unit may have mutual magnetic poles opposed to each other along a movement direction of the locking unit so that attractive and repulsive forces are applied in directions perpendicular to the locking and release directions.

Also, the first magnetic force unit may include a movable magnet unit that moves in the locking direction and the release direction, the second magnetic force unit may include a plurality of stationary magnet units spaced a preset distance from each other in a horizontal direction while being relatively fixed with respect to movement of the first magnetic force unit, and the movable magnet unit may be moved to a release position at which a repulsive force with the second stationary magnet unit is applied by movement as many as the preset distance in the release direction from a locking position at which an attractive force with the first stationary magnet unit is applied.

Also, the arrangement number of the stationary magnet units may be two times greater than that of the movable magnet unit, and the attractive force and the repulsive force may further increase as the mutual magnetic poles are arranged opposed to each other at the locking position and the release position.

Also, an apparatus for locking a surgical instrument by using magnetic force, characterized by including: a rotating locking unit configured to be moved and rotated in order to: apply an attractive force and a repulsive force according to movements in a locking direction and a release direction, respectively; lock a surgical instrument by formation of a locking magnetic force caused by the attractive force; and unlock the surgical instrument by formation of a release magnetic force caused by the repulsive force; a rotating body unit having a space into which the rotating locking unit is moved in the locking direction and the release direction and configured to transmit a transmitted driving force to the surgical instrument; a stationary locking unit configured to interact with the rotating locking unit to form the locking magnetic force and the release magnetic force; and a stationary body unit configured to transmit the driving force to the rotating body unit and comprising the stationary locking unit therein.

Also, the rotating locking unit may include a movable magnet unit moved in the locking direction and the release direction according to body movement of the rotating locking unit, the stationary locking unit may include a plurality of stationary magnet units spaced a preset distance from each other while being relatively fixed with respect to movement of the rotating locking unit, and locking of the rotating locking unit may be released by a repulsive force as the movable magnet unit is moved as many as a preset distance from a locking position at which an attractive force with the first stationary magnet unit is applied to a release position at which a repulsive force with the second stationary magnet unit is applied in the release direction.

Also, the plurality of stationary magnet units have magnetic poles that are alternately arranged along a movement direction so as to form the locking magnetic force and the release magnetic force in the locking direction and the release direction of the rotating locking unit.

Also, the movable magnet unit and the plurality of stationary magnet units may have mutual magnetic poles opposed to each other along a movement direction of the locking unit so that attractive and repulsive forces are applied in directions perpendicular to the locking and release directions.

Also, the stationary body unit may include: a surgical instrument holder having a 'U'-shaped hinge groove, in an end thereof, by which a coupling unit extending upward from an end of the stationary body unit to couple the surgical instrument with the rotating body unit is supported and mounted, so that the surgical instrument is inserted and installed in the 'U'-shaped hinge groove in a rear-to-front direction, and locking of the surgical instrument is released as the rotating locking unit is rotated by using the 'U'-shaped hinge groove as a rotation axis according to the release magnetic force; and a rotating body support extending upward from a position spaced a predetermined distance from the surgical instrument holder in the horizontal direction to support the rotating body unit.

Also, the stationary body unit may include: a first stationary magnet seated groove in which the first stationary magnet unit is inserted and seated; and a second stationary magnet seated groove which is spaced a preset distance from the first stationary magnet seated groove and in which the second stationary magnet unit is inserted and seated, and in the first and second stationary magnet seated grooves, mutual magnetic poles of the first and second stationary magnet units and the movable magnet unit may be arranged opposed to each other along a movement direction of the rotating locking unit so that an attractive force and a repulsive force are applied in a direction perpendicular to the locking direction and the release direction.

Also, the rotating locking unit may be rotated at a preset angle by using the 'U'-shaped hinge groove as a rotation axis by a release magnetic force formed in a vertical direction to a release direction as horizontally moved in the release direction to release the locking, and the surgical instrument may be uninstalled from the 'U'-shaped hinge groove in a front-to-rear direction as the locking of the rotating locking unit is released.

Advantageous Effects

According to the above-described present invention, the effects of maximally reducing the load that occurs during installing/uninstalling the instrument for microsurgery are obtained.

BRIEF DESCRIPTION OF THE DRAWINGS

The following drawings attached in this specification illustrate a preferred embodiment of the present invention and function to make further understood the technical spirit of the present invention along with the detailed description of the invention, and thus, the present invention should not be construed as being limited to only the drawings. In the drawings:

FIG. 10 is a view illustrating a state in which a magnetic pole direction of the movable magnet unit is formed in a horizontal direction according to an embodiment of the present invention.

MODE FOR CARRYING OUT THE INVENTION

Hereinafter, a preferred embodiment of the present invention will be described with reference to the accompanying drawings. The present disclosure may, however, be embodied in different forms and should not be construed as limited to the embodiments set forth herein. Rather, these embodiments are provided so that this disclosure will be thorough and complete, and will fully convey the scope of the inventive concept to those skilled in the art. Moreover, detailed descriptions related to well-known functions or configurations will be ruled out in order not to unnecessarily obscure subject matters of the present invention. It will be apparent to those skilled in the art that various modifications and variations can be made in the present invention without departing form the spirit or scope of the invention.

An apparatus for locking a surgical instrument by using magnetic force according to an embodiment of the present invention performs a locking operation and unlocking operation on a surgical instrument 10 by using attractive force and repulsive force when the surgical instrument 10 is locked to or unlocked from an object to be locked. Hereinafter, the apparatus for locking a surgical instrument by using magnetic force according to an embodiment of the present invention will be described in detail with reference to the accompanying drawings.

Figure 5:
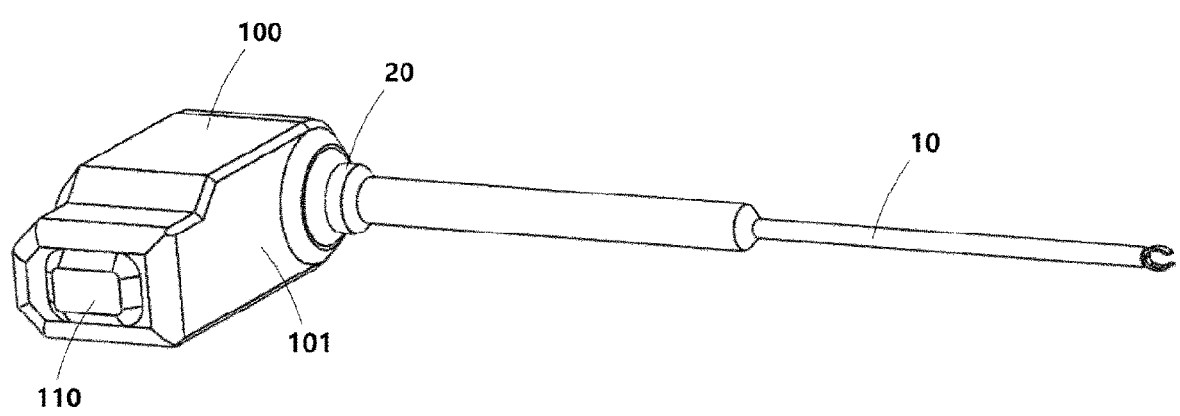
FIG. 5 is a view illustrating a state in which a rotating body unit 100 and a surgical instrument 10 are coupled by a coupling unit 20 according to an embodiment of the present invention.
Figure 8:
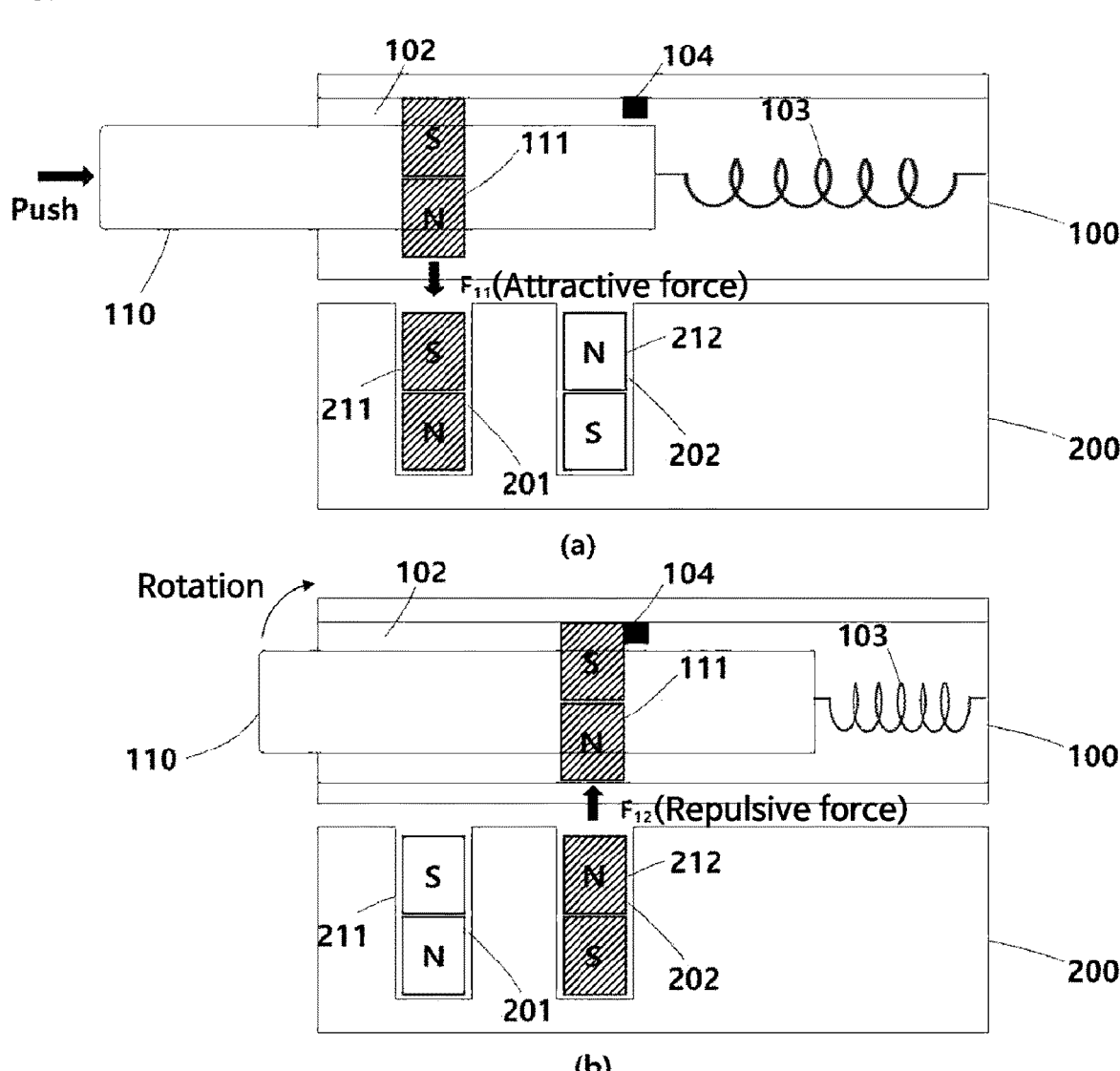
FIG. 8 is a view illustrating a state in which an attractive force and a repulsive force are generated between a movable magnet unit 111 and first and second stationary magnet units 211 and 212, which form magnetic poles in a vertical direction, according to an embodiment of the present invention.

As illustrated in FIGS. 1 to 4, a rotating body unit 100 according to an embodiment of the present invention is coupled with the surgical instrument 10 through a coupling unit 20. The rotating body unit 100 extends in a horizontal direction, and the coupling unit 10 has one end coupled to a front body 101 and the other end coupled to the surgical instrument 10 as illustrated in FIG. 5. As illustrated in FIG. 8, a movement groove 102 is formed in the rotating body unit 100 in a longitudinal direction thereof so that a rotating locking unit 110 is movable in the horizontal direction.

An elastic unit 103 is disposed inside the rotating body unit 100 to provide elasticity to the rotating locking unit 110 when the rotating locking unit 110 is moved along the movement groove 102 by an external force in the horizontal direction (or release direction). Accordingly, the rotating locking unit 110 is moved to a release position by elasticity of the elastic unit 103 disposed in an elastic space of the rotating body unit 100 when an external force is pushed to the rotating locking unit 110 as illustrated in (b) of FIG. 8 and returned to a locking position by the elasticity when the external force is removed as illustrated in (a) of FIG. 8. Here, when an external force is applied to the rotating locking unit 110 as an example for explaining the present invention, the rotating locking unit 110 may be moved in the horizontal direction (release direction) and caught and fixed by a hook device (not shown) as illustrated in (b) of FIG. 8 and returned to an original position again when the fixing of the hook device is released by an external force as illustrated in (a) of FIG. 8.

A stopper unit 104 may be disposed in one area inside the rotating body unit 100 to exactly move a position as which a release magnetic force (or repulsive force) is generated while the rotating locking unit 110 is moved in the release direction as illustrated in (b) of FIG. 8. The stopper unit 104 disposed inside the rotating body unit 100 restricts the movement of the rotating locking unit 110 in the release direction, so that a magnet of the rotating locking unit is disposed at a release position at which a repulsive force is applied.

On the other hand, the rotating locking unit 110 is moved along the movement groove 102 in the release direction when an external force is applied to the rotating locking unit 110 or returned to an original position again in the locking direction when the external force is removed. Here, a horizontal movement assistant member may be disposed along a longitudinal direction of the movement groove 102 to allow the rotating locking unit 110 to be horizontally moved in the release direction or the locking direction.

The rotating locking unit 110 according to an embodiment of the present invention is horizontally moved in a direction in which an external force is applied when an external force pushing in the horizontal direction is applied as described above. As illustrated in FIG. 8, a movable magnet unit 111 (or first magnetic force unit) having different magnetic poles (N pole and S pole) is inserted and coupled to the rotating locking unit 110 in a circumferential direction of a body thereof. Thus, the movable magnet unit 111 interacts with a plurality of stationary magnet units 211 and 212 that will be described later to form an attractive force and a repulsive force. Here, a state in which the movable magnet unit 111 is disposed as illustrated in (a) of FIG. 8 indicates the locking position at which an attractive force interacts, and a state in which the movable magnet unit 111 is disposed as illustrated in (b) of FIG. 8 indicates the release position at which a repulsive force interacts.

Figure 1:
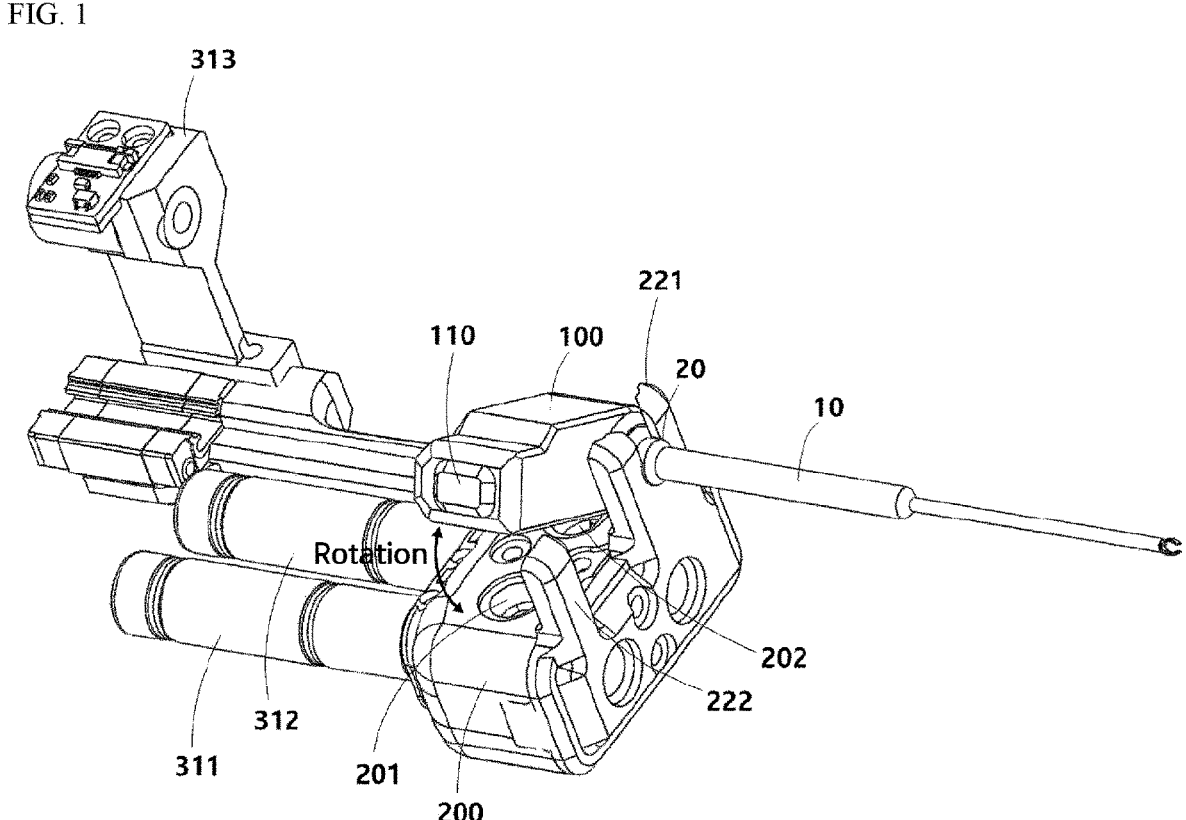
FIGS. 1 to 4 are views illustrating an apparatus for locking a surgical instrument by using magnetic force according to an embodiment of the present invention.

When the rotating locking unit 110 is disposed at the release position, the rotating body unit 100 and the rotating locking unit 110 may be rotated at a preset angle as illustrated in FIG. 1 by the repulsive force, and thus the surgical instrument 10 is unlocked.

As illustrated in FIGS. 1 to 4, the stationary body unit 200 according to an embodiment of the present invention is disposed below the rotating body unit 100. The stationary body unit 200 includes first and second stationary magnet seated grooves 201 and 202 and first and second shaft insertion grooves 205 and 206.

The first and second stationary magnet seated grooves 201 and 202 and the first and second shaft insertion grooves 205 and 206 are formed in a top surface of the stationary body unit 200. The first and second stationary magnet units 211 and 212 that will be described later are inserted and seated in the first and second stationary magnet seated grooves 201 and 202. The first and second stationary magnet seated grooves 201 and 202 are formed at the release position and the locking position so that the attractive force and the repulsive force are formed therein, respectively, by interacting with the first and second stationary magnet units 211 and 212 depending on the locking position or the release position of the movable magnet unit 111. That is, when the movable magnet unit 111 is disposed at the locking position as illustrated in (a) of FIG. 8, the first stationary magnet seated grooves 201 may be formed on the same virtual vertical line with the movable magnet unit 111. Also, when the movable magnet unit 111 is in the release position as illustrated in (b) of FIG. 8, the second stationary magnet seated grooves 202 may be formed on the same virtual vertical line with the movable magnet unit 111. Thus, the first and second stationary magnet units 211 and 212 inserted and seated in the first and second stationary magnet seated grooves 201 and 202 and the movable magnet unit 111 face each other to form the attractive force and the repulsive force respectively, when the first and second stationary magnet seated grooves 201 and 202 is respectively formed in the locking position or the release position of the movable magnet unit 111.

A stationary locking unit 210 according to an embodiment of the present invention interacts with the rotating locking unit 110 to form a locking magnetic force (the attractive force) and a release magnetic force (the repulsive force). The stationary locking unit 210 includes the first stationary magnet unit 211 (a second magnetic force unit) and the second stationary magnet unit 212 (the second magnetic force unit). The first and second stationary magnet units 211 and 212 are respectively inserted and seated into the first and second stationary magnet seated grooves 201 and 202 while having different magnetic poles (N pole and P pole) as illustrated in (a) of FIG. 8. The first stationary magnet unit 211 is inserted and fixed in the first stationary magnet seated groove 201 so that the upper side becomes the S pole, and the second stationary magnet unit 212 is inserted and fixed in the second stationary magnet seated groove 202 so that the upper side becomes the N pole as illustrated in (a) of FIG. 8. The movable magnet unit 111 interacting with the first and second stationary magnet units 211 and 212 is disposed in the locking position so that the lower side becomes the N pole. Accordingly, the N pole of the movable magnet unit 111 and the S pole of the first stationary magnet units 211 interact with each other to generate an attractive force F11 in the locking position. The rotating body unit 100 is locked by the generated attractive force, and the surgical instrument 10 coupled to the rotating body unit 100 is installed by the locking of the rotating body unit 100.

On the other hand, the movable magnet unit 111 moves in the horizontal direction to be located in the locking position, when an external force out of the attractive force is pushed to the rotating locking unit 110 in the horizontal direction as illustrated in (b) of FIG. 8. The N pole of the movable magnet unit 111 and the N pole of second stationary magnet units 212 interact with each other to generate a repulsive force F12 in the release position. The rotating body unit 100 is unlocked by the generated repulsive force, the rotating body unit 100 by the unlocking may be rotated at a predetermined angle in the clockwise direction as illustrated in FIG. 1, accordingly the surgical instrument 10 coupled to the rotating body unit 100 is uninstalled.

The above-described magnetic pole direction is not limited thereto. For example, the magnetic pole directions of the plurality of stationary magnet units 211 and 212 corresponding to the magnetic pole direction of the movable magnet unit 111 may be set in consideration that the attractive force and the repulsive force are applied.

When one permanent magnet is arranged as the movable magnet unit 111 as illustrated in FIG. 8, two permanent magnets may be arranged as the plurality of stationary magnet units. When two permanent magnets are arranged as the movable magnet unit 111 as illustrated in FIG. 8, two permanent magnets may be arranged as the plurality of stationary magnet units.

Figure 9:
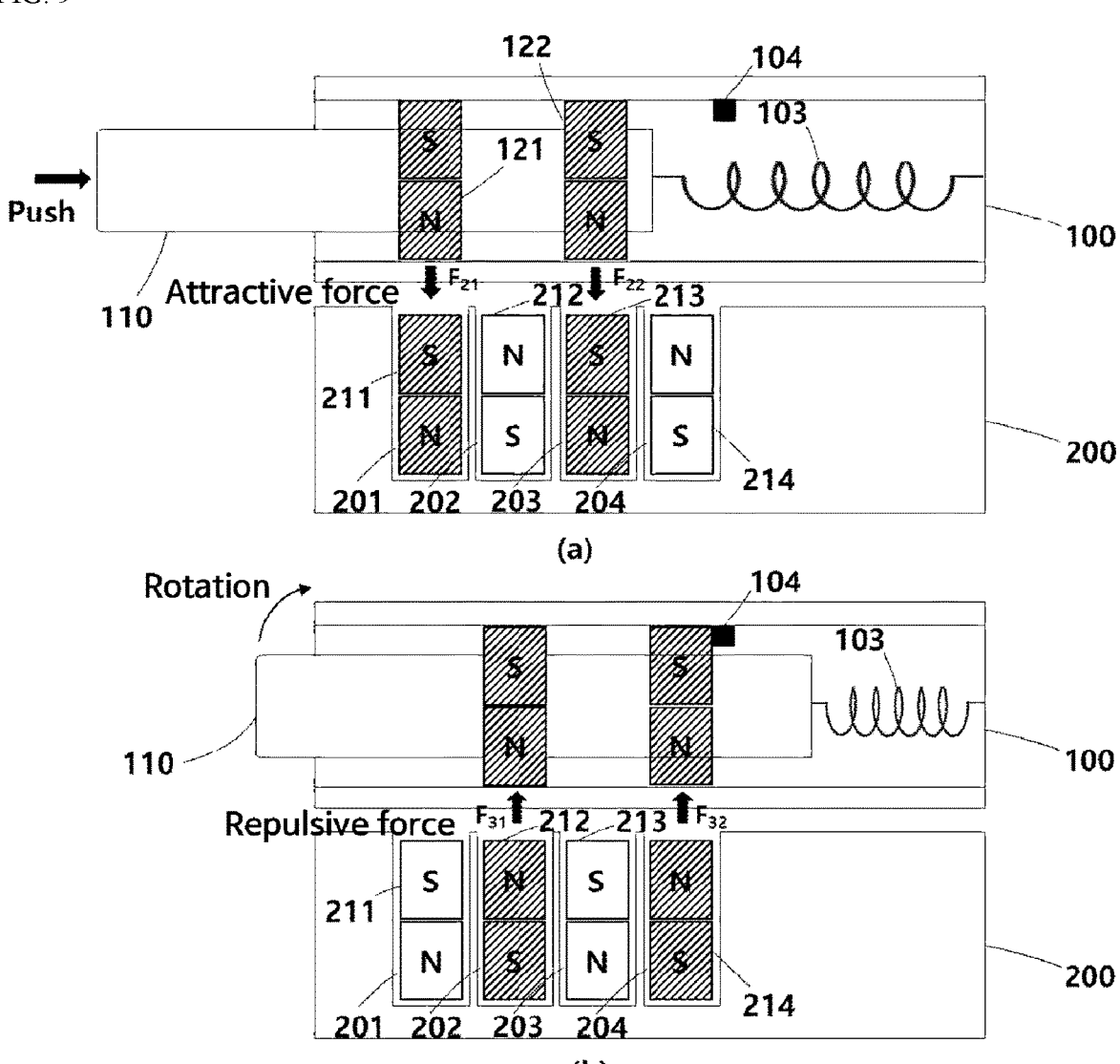
FIG. 9 is a view illustrating a state in which an attractive force and a repulsive force are generated between first and second movable magnet unit 121,122 and first, second, third, and fourth stationary magnet units 211, 212, 213, and 214, which form magnetic poles in the vertical direction, according to an embodiment of the present invention.

As illustrated in (a) of FIG. 9, first and second movable magnet units 121 and 122 spaced a preset distance from each other are inserted and coupled in the circumferential direction of the body of the rotating locking unit 110. Here, the spaced distance is determined in consideration of a locking position and a release position of the first and second movable magnet units 121 and 122 and in consideration that attractive and repulsive forces are applied. Each of first, second, third, and fourth stationary magnet units 211, 212, 213, and 214 is disposed below the first and second movable magnet units 121 and 122 in correspondence thereto. The first, second, third and fourth stationary magnet units 211, 212, 213 and 214 are inserted and fixed to first, second, third and fourth stationary magnet seated grooves 201, 202, 203 and 204, respectively. When the first and second movable magnet units 121 and 122 are in the locking position as illustrated in (a) of FIG. 9, the first and second movable magnet units 121 and 122 are arranged to have magnetic poles facing those of the first and third stationary magnet units 211 and 213, and attractive forces F21 and F22 act therebetween. Thus, the first and second movable magnet units 121 and 122 and the first and third fixed magnet units 211 and 213 are disposed on the same virtual vertical line. The rotating body unit 100 is locked by the generated attractive force, and the surgical instrument 10 coupled to the rotating body unit 100 is installed by the locking of the rotating body unit 100. Here, the generated attractive forces F21 and F22 have a magnetic force greater than that of the attractive force F11 in FIG. 8.

When an external force greater than the attractive forces F21 and F22 is applied to the rotating locking unit 110 in the horizontal direction as illustrated in (b) of FIG. 9, the first and second movable magnet units 121,122 are moved in the horizontal direction and disposed at the release position. At the release position, the first and second movable magnet units 121 and 122 and the second and fourth stationary magnet units 212 and 214 interact with each other to generate repulsive forces F31 and F32. When the rotating body unit 100 is unlocked by the generated repulsive force, the rotating body unit 100 may be rotated by the unlocking of the rotating body unit 100 at a predetermined angle in the clockwise direction as illustrated in FIG. 1, and accordingly, the surgical instrument 10 coupled to the rotating body unit 100 is uninstalled. Here, the generated attractive forces F31 and F32 have a magnetic force greater than that of the attractive force F12 in FIG. 8.

As described above, the first, second, third, and fourth stationary magnet units 211, 212, 213, and 214 are arranged to have magnetic poles that are sequentially alternated with each other, and the first and second movable magnet units 121 and 122 are arranged to have the same magnetic pole as each other. The magnetic force may be further increased by arranging twice as many stationary magnet units as the number of the movable magnet units.

Figure 10:
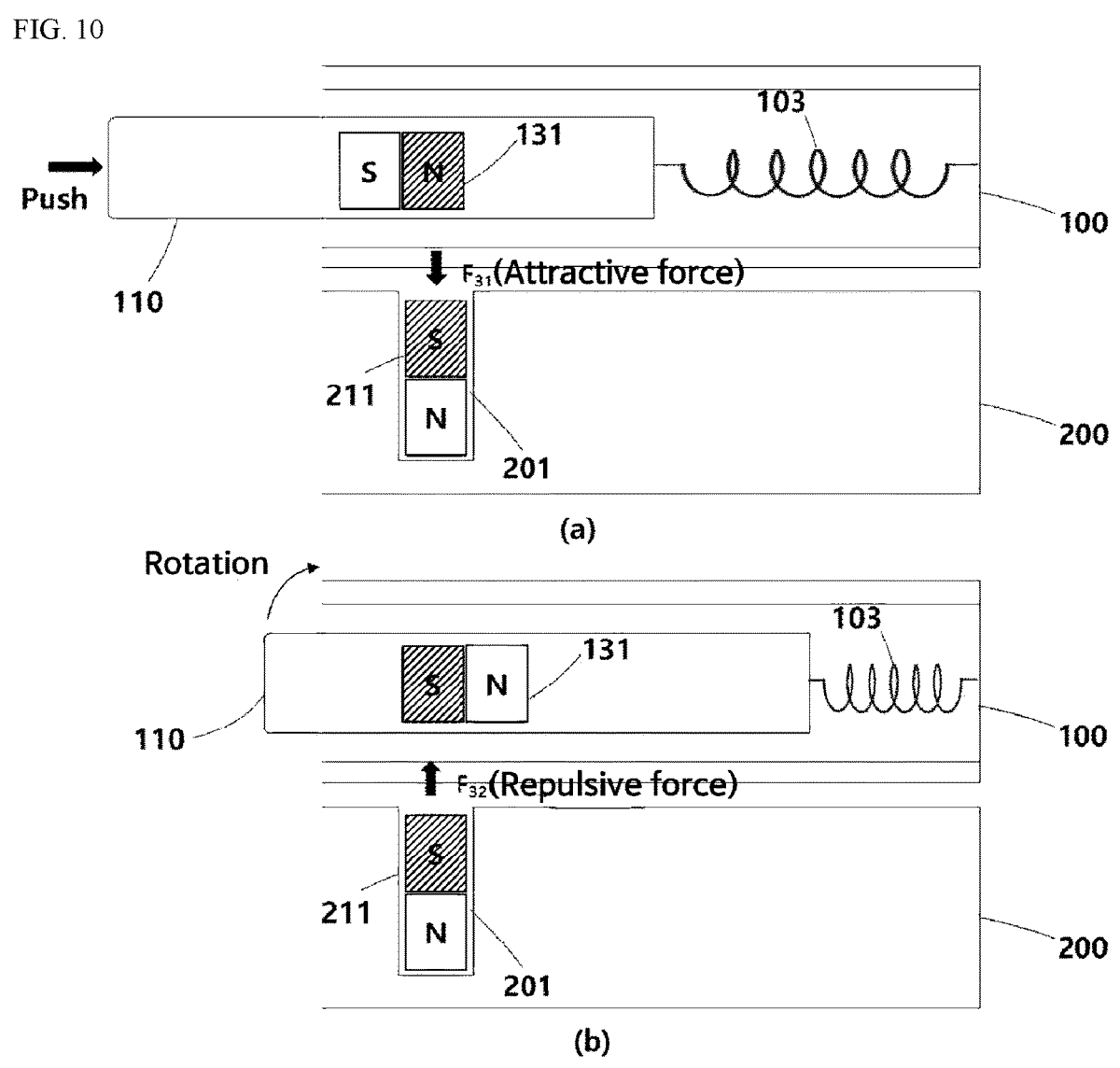

As illustrated in FIG. 10, a movable magnet unit 131 is arranged so that S and N poles are formed in the horizontal direction unlike FIGS. 8 and 9. That is, the movable magnet units 111, 121, and 122 of FIGS. 8 and 9 are arranged so that the S pole and the N pole are formed in the vertical direction, and the movable magnet unit 131 of FIG. 10 is arranged so that the S pole and the N pole are formed in the horizontal direction. As the magnetic pole of the movable magnet unit 131 is formed in the horizontal direction, one stationary magnet unit 211 corresponding to the movable magnet unit 131 may be arranged as illustrated in FIG. 10, and two stationary magnet units 211 may be arranged to further increase the repulsive force. That is, in order to further increase the repulsive force, an additional second stationary magnet unit (not shown) spaced a predetermined distance from the first stationary magnet unit 211 to have opposite directions of magnetic poles may be arranged.

In (a) of FIG. 10, the attractive force F31 acts between the movable magnet unit 131 and the stationary magnet unit 211 to form a locking magnetic force, and in (b) of FIG. 10, as the movable magnet unit 131 is moved in the horizontal direction, the repulsive force F32 acts between the movable magnet unit 131 and the stationary magnet unit 211 to form a release magnetic force.

Also, although not shown in the drawings, a plurality of movable magnet units are spaced a predetermined distance from each other in the horizontal direction, and the stationary magnet units corresponding to the movable magnet units in pairs are arranged based on the arrangement of the movable magnet unit to form the attractive and repulsive forces in pairs, thereby increasing the attractive force and the repulsive force at the same time.

Figure 6:
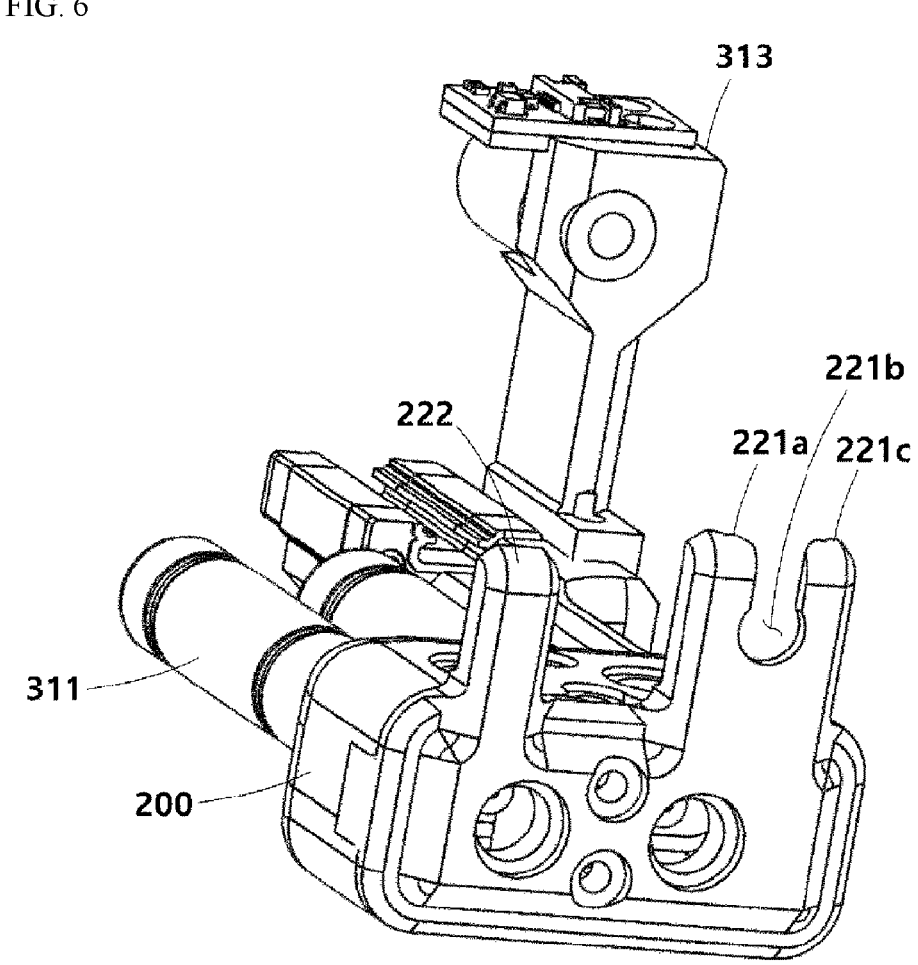
FIGS. 6 and 7 are views illustrating a state in which a "U"-shaped hinge groove is formed in an upper end of a surgical instrument holder 221 according to an embodiment of the present invention.
Figure 7:
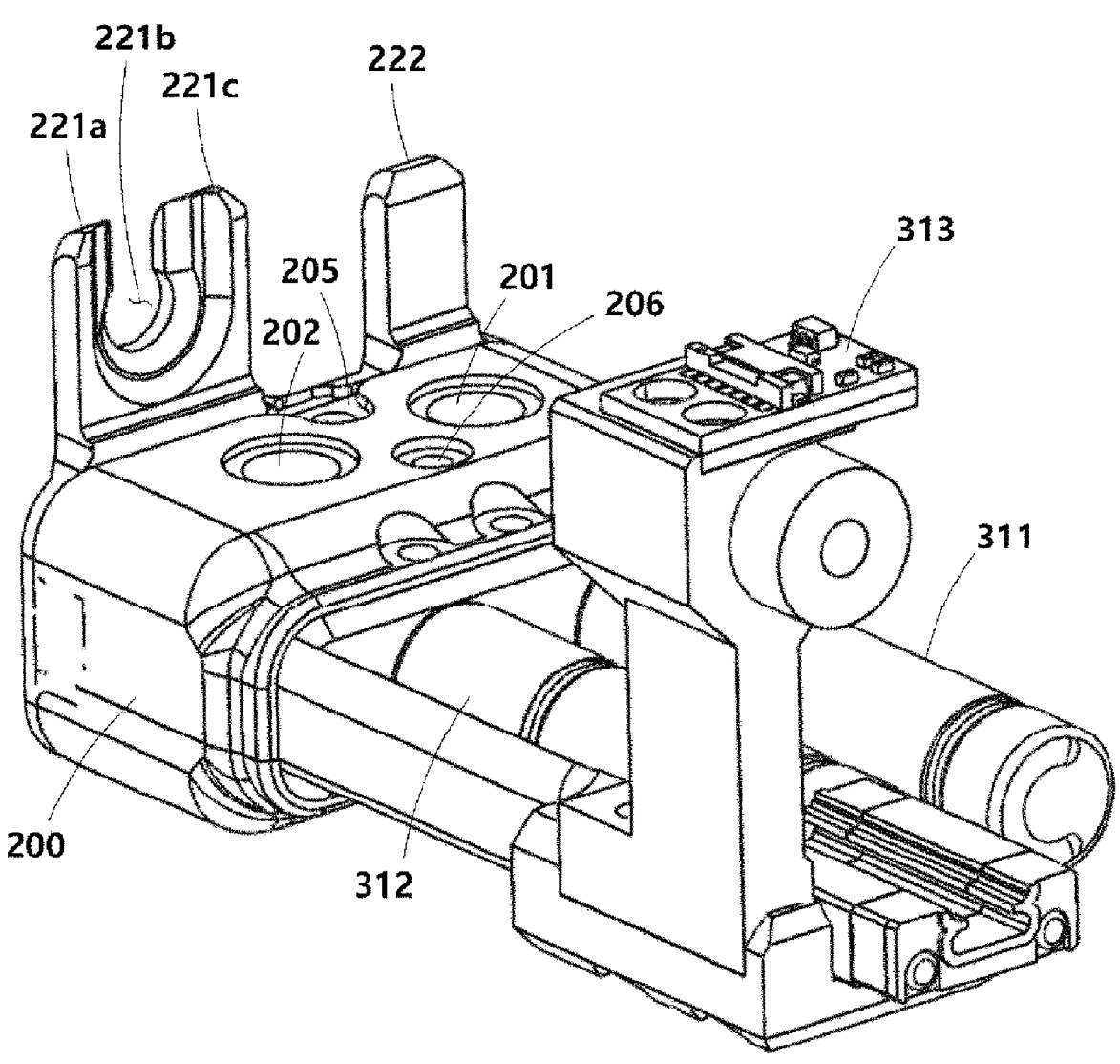

As illustrated in FIGS. 1, 6, and 7, a surgical instrument holder 221 according to an embodiment of the present invention extends upward from an end of the stationary body unit 200, and a hinge groove 221b having a shape of 'U' is formed at an upper central end. As illustrated in FIG. 1, the coupling unit 20 for coupling the rotating body unit 100 and the surgical instrument 10 is supported and mounted in the 'U'-shaped hinge groove 221b. As the rotating locking unit 110 is unlocked as described above, the rotating locking unit 110 is rotated in the clockwise direction by using the 'U'-shaped hinge groove 221b as a rotation axis. That is, the coupling unit 20 is rotated in the clockwise direction in the 'U'-shaped hinge groove 221b. The surgical instrument 10 is inserted and installed in the 'U'-shaped hinge groove in a rear-to-front direction and is uninstalled from the 'U'-shaped hinge groove in a front-to-rear direction.

Figure 2:
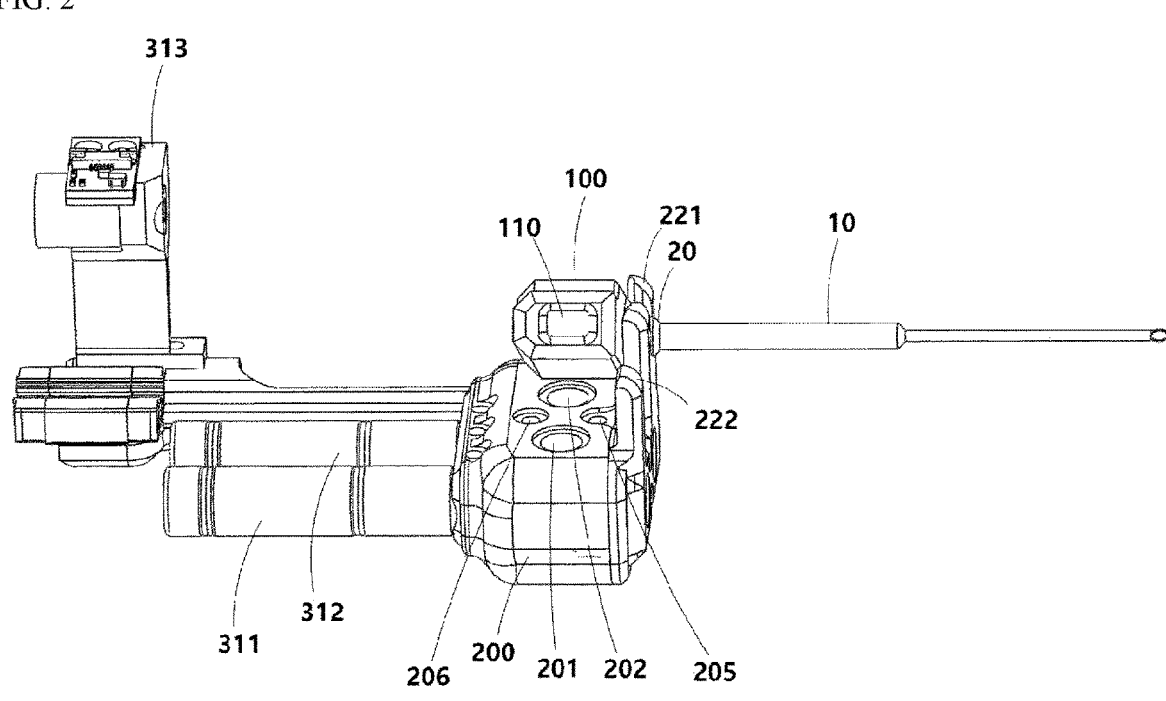
Figure 3:
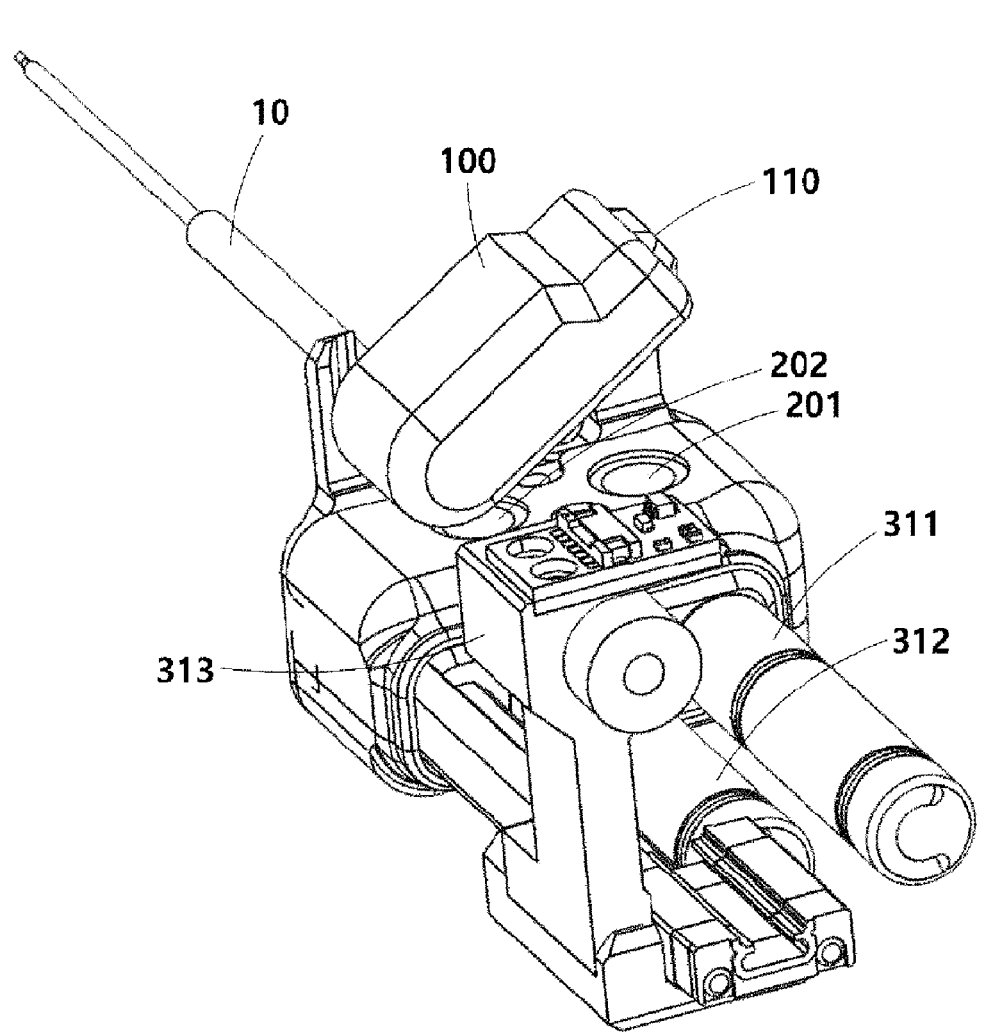
Figure 4:
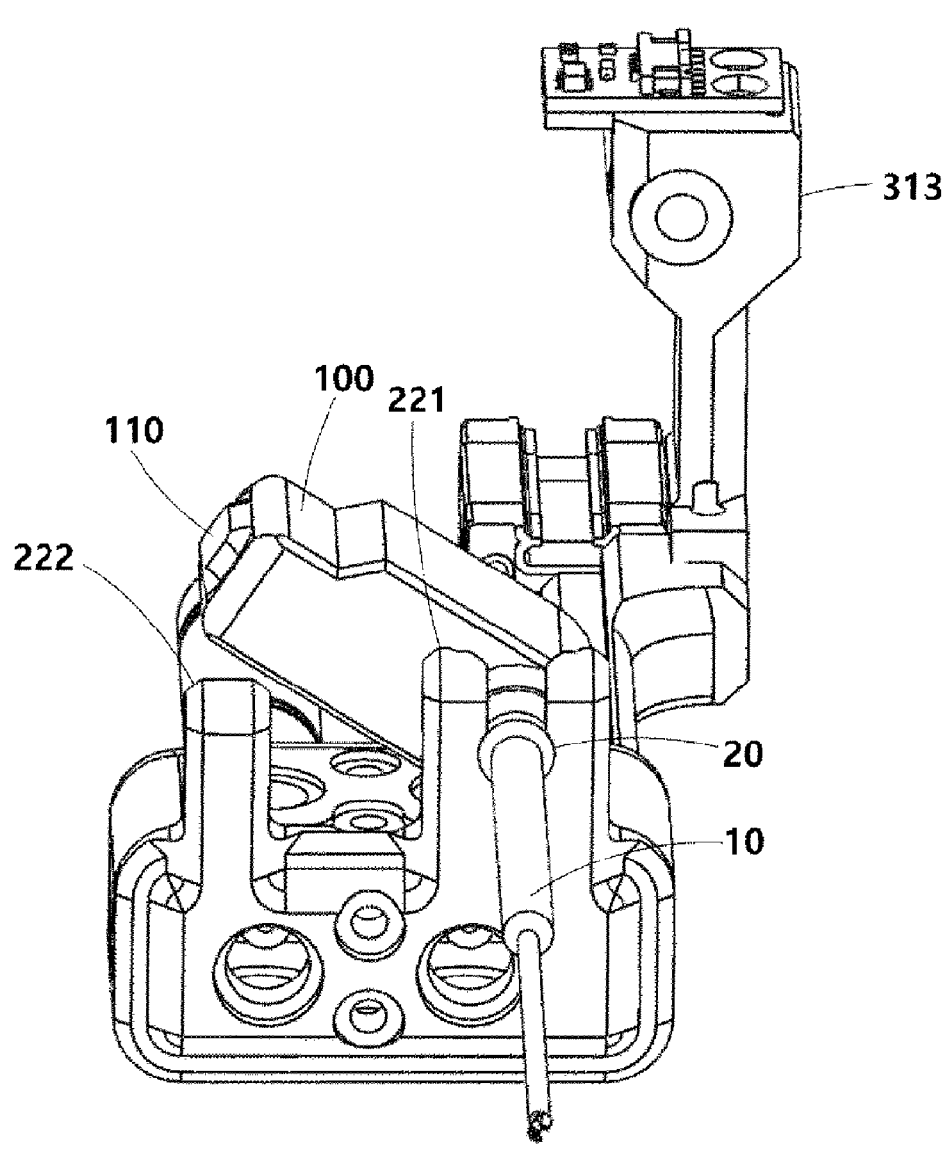

A rotating body unit support 222 according to an embodiment of the present invention extends upward at a position spaced a predetermined distance from the surgical instrument holder 221 in the horizontal direction to support the rotating body unit 100 that is rotating. That is, the rotating body unit 100 is rotated in the clockwise or counterclockwise direction when installed or uninstalled, and at this time, as illustrated in FIG. 2, the rotating body unit 100 supports a rotational movement of the rotating body unit 100.

Each of first and second power transmission devices 311 and 312 in FIG. 1 includes a motor and a gear to transmit a driving force to first and second shafts (not shown) inserted and fixed to first and second shaft insertion grooves 205 and 206, respectively. The first and second shafts transmit the received driving force to the rotating body unit 100, thereby finally transmitting the driving force to the surgical instrument 10. The surgical instrument 10 may perform shaft rotation and grasping as the first and second power transmission devices 311 and 312 are driven. A third power transmission device 313 transmits a driving force when the surgical instrument 10 is moved forward or backward.

In describing the present invention, descriptions of related art and matters obvious to those skilled in the art can be omitted, and descriptions of these omitted components (methods) and functions will be sufficiently referred to within a range without departing from the scope and spirit of the invention. It is also understood that the above-described components of the present invention have been described for convenience of description, but components that have not been described herein can be added within a range without departing from the scope and spirit of the invention.

The component and function of each part described above have been separately described for convenience of explanation, but any one component and function may be integrated with or divided into other components as necessary.

Although the embodiments of the present invention have been described, it is understood that the present invention should not be limited to these embodiments but various changes and modifications can be made by one ordinary skilled in the art within the spirit and scope of the present invention as hereinafter claimed. Moreover, detailed descriptions related to well-known functions or configurations will be ruled out in order not to unnecessarily obscure subject matters of the present invention.

The invention claimed is:

1. An apparatus for locking a surgical instrument by using magnetic force, characterized by comprising:

a rotating locking unit configured to be moved and rotated in order to: apply an attractive force and a repulsive force according to movements in a locking direction and a release direction, respectively; lock a surgical instrument by formation of a locking magnetic force caused by the attractive force; and unlock the surgical instrument by formation of a release magnetic force caused by the repulsive force;

a rotating body unit having a space into which the rotating locking unit is moved in the locking direction and the release direction and configured to transmit a transmitted driving force to the surgical instrument;

a stationary locking unit configured to interact with the rotating locking unit to form the locking magnetic force and the release magnetic force; and a stationary body unit configured to transmit the driving force to the rotating body unit and comprising the stationary locking unit therein, wherein the stationary body unit comprises:

a surgical instrument holder having a hinge groove, in an end thereof, by which a coupling unit extending upward from an end of the stationary body unit to couple the surgical instrument with the rotating body unit is supported and mounted, so that the surgical instrument is inserted and installed in the hinge groove in a rear-to-front direction, and locking of the surgical instrument is released as the rotating locking unit is rotated by using the hinge groove as a rotation axis according to the release magnetic force; and a rotating body support extending upward from a position spaced a predetermined distance from the surgical instrument holder in the horizontal direction to support the rotating body unit.

2. The apparatus of claim 1, characterized in that the rotating locking unit comprises a movable magnet unit moved in the locking direction and the release direction according to body movement of the rotating locking unit, the stationary locking unit comprises a plurality of stationary magnet units spaced a preset distance from each other while being relatively fixed with respect to movement of the rotating locking unit, and locking of the rotating locking unit is released by a repulsive force as the movable magnet unit is moved as many as a preset distance from a locking position at which an attractive force with the first stationary magnet unit is applied to a release position at which a repulsive force with the second stationary magnet unit is applied in the release direction.

3. The apparatus of claim 2, characterized in that the plurality of stationary magnet units have magnetic poles that are alternately arranged along a movement direction so as to form the locking magnetic force and the release magnetic force in the locking direction and the release direction of the rotating locking unit.

4. The apparatus of claim 3, characterized in that the movable magnet unit and the plurality of stationary magnet units have mutual magnetic poles opposed to each other along a movement direction of the locking unit so that attractive and repulsive forces are applied in directions perpendicular to the locking and release directions.

5. The apparatus of claim 2, characterized in that the stationary body unit comprises:

a first stationary magnet seated groove in which the first stationary magnet unit is inserted and seated; and a second stationary magnet seated groove which is spaced a preset distance from the first stationary magnet seated groove and in which the second stationary magnet unit is inserted and seated, wherein in the first and second stationary magnet seated grooves, mutual magnetic poles of the first and second stationary magnet units and the movable magnet unit are arranged opposed to each other along a movement direction of the rotating locking unit so that an attractive force and a repulsive force are applied in a direction perpendicular to the locking direction and the release direction.

6. The apparatus of claim 1, characterized in that the rotating locking unit is rotated at a preset angle by using the 'U'-shaped hinge groove as a rotation axis by a release magnetic force formed in a vertical direction to a release direction as horizontally moved in the release direction to release the locking, and the surgical instrument is uninstalled from the 'U'-shaped hinge groove in a front-to-rear direction as the locking of the rotating locking unit is released.

* * * * *